US00RE33901E

United States Patent [19]

Shinjo

[11] E Patent Number: Re. 33,901

[45] Reissued Date of Patent: Apr. 28, 1992

[54] BREAKABLE COMPOSITE DRILL SCREW

[75] Inventor: Katsumi Shinjo, Osaka, Japan

[73] Assignee: Yugen Kaisha Shinjoseisakusho, Osaka, Japan

[21] Appl. No.: 685,260

[22] Filed: Apr. 11, 1991

Related U.S. Patent Documents

Reissue of:

[64] Patent No.: 4,958,972
Issued: Sep. 25, 1990
Appl. No.: 430,845
Filed: Nov. 1, 1989

[30] Foreign Application Priority Data

Nov. 25, 1988 [JP] Japan ..... 63-297334

[51] Int. Cl.[5] ..... F16B 25/00; F16B 31/00

[52] U.S. Cl. ..... 411/387; 411/5; 411/900

[58] Field of Search ..... 411/2-5, 411/386, 387, 396, 383, 171, 900; 10/10 R

[56] References Cited

U.S. PATENT DOCUMENTS 910,434 1/1909 Thompson ..... 411/900

FOREIGN PATENT DOCUMENTS 2549147 5/1977 Fed. Rep. of Germany ..... 411/387

*Primary Examiner*—Neill R. Wilson
*Attorney, Agent, or Firm*—Jordan and Hamburg

[57] ABSTRACT

A breakable composite drill screw comprises a first shank made of a metal unsusceptible of hardening, a driving head extending from one end of the first shank and engageable with a screw driving tool, a second shank made of another metal susceptible of hardening, the second shank being fixedly adjoined to the other end of the first shank to thereby provide a break zone at said other end, a drill bit formed by cold forging at an end of the second shank, a continuous thread formed by thread-rolling to extend around both outer cylindrical peripheries of the first and second shank wherein a portion extending from the break zone to the drill bit is hardened or quenched, and wherein said shanks are adjoined at their engaging surfaces to each other by projection-welding technique making use of a welding lug protruding from either engaging surface, said lug forming the break zone.

3 Claims, 1 Drawing Sheet

BREAKABLE COMPOSITE DRILL SCREW

Matter enclosed in heavy brackets [ ] appears in the original patent but forms no part of this reissue specification; matter printed in italics indicates the additions made by reissue.

BACKGROUND OF THE INVENTION

The present invention relates to a breakable composite drill screw which can be snapped in two in such a manner that a drill bit or chip and a superfluous threaded stem portion adjoined thereto are broken off to be removed from the drill screw after it has been turned tight.

A so-called drill screw which has a drill bit formed at a tip end of a screw having a driving head is advantageous in that the forming of holes in workpieces to be fastened, tapping of the holes and fastening of the workpieces with the screw can be carried out in one continuous operation. Therefore, the range of its use is rapidly increasing. As new and various uses are found for such drill screw, there arises a certain problem in some cases. For example, the drill bit and a superfluous portion of threaded stem adjoining said drill bit protrude from a back surface of a structure after it has been fastened by the drill screw, thereby spoiling the beauty of the structure or building and further being likely to inflict an injury on a person. This has led to a serious demand for an improved drill screw which after fastening thereof permits its protruding super fluous portions to be broken and removed from its main portion.

In this regard, it is a common practice to form a groove at a point where a screw is to be broken to remove such protruding superfluous portions. However, such a common practice cannot be applied to aforementioned drill screws because they have previously been so hardened as to have sufficient hardness for the machining or cutting of their drill bits and also for the tapping of their threaded stems adjoining the drill bits. The thus hardened surface makes it difficult to break the screw at such grooved portion thereof.

SUMMARY OF THE INVENTION

It is therefore an object of the present invention to provide a drill screw which is formed with a drill bit and a threaded stem adjacent thereto wherein the drill bit and an end portion of the threaded stem which will protrude from a back surface of a structure fastened with the drill screw are easily broken and removed without failure.

The object is accomplished in the invention by employing in the drill screw a new composite structure comprising: a first shank made of a metal unsusceptible of hardening; a driving head extending from one end of the first shank so as to be engageable with a screw driving tool; a second shank made of another metal susceptible of hardening, the second shank being fixedly adjoined at a point to the other end of the first shank in such a manner that a break zone is provided at the point; a drill bit formed by cold forging at an end of the second shank; a continuous thread formed by thread-rolling technique to extend around both outer cylindrical peripheries of the first and second shanks, wherein a portion extending from the break zone to the drill bit is hardened or quenched.

It is preferable to employ projection-welding technique in order to cause the first shank to fixedly adjoin the second shank by means of a welding lug protruding from one of contacting surfaces of the shanks.

It is also desirable that the continuous thread which is formed by the thread-rolling technique on a section of the second shank near the drill bit comprises at least one pitch of screw thread.

For practical purposes, it is advantageously effective to use an austenitic stainless steel as a material of the first shank and at the same time to use a low-carbon steel as a material of the second shank.

The drill screw which in accordance with the invention has such a structure as described above enables easier and neater breaking or snapping and subsequent removal of the drill bit and superfluous threaded portion which will project from back surface of a fastened object.

DETAILED DESCRIPTION OF THE INVENTION

Figure 1:
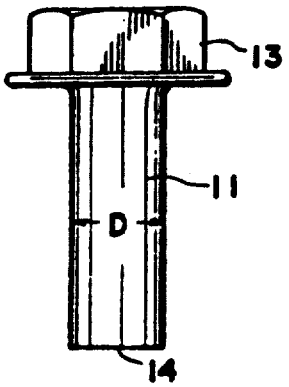
FIG. 1 is a front elevation showing a first shank.
Figure 2:
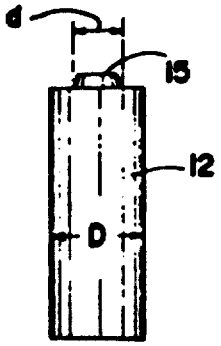
FIG. 2 is a front elevation showing a second shank.

An embodiment of the invention will now be described referring to the drawings in which FIG. 1 shows a first shank 11 constituting a drill screw according to the invention, and FIG. 2 shows a second shank 12 also constituting the drill screw.

The first shank 11 is made of austenitic stainless steel which is a metal unsusceptible of carburizing-and-quenching, and is of a predetermined diameter 'D' suited to thread-rolling formation of screw thread as described hereinafter. The first shank 11 has at its end a driving head 13 which is formed by header-machining technique to be of a shape engageable with a screw driving tool, whereas another end of said first shank 11 is machined to a flat surface 14.

The second shank 12 is made of a metal of another kind, for instance of a low-carbon steel which is susceptible of carburizing-and-quenching, the second shank 12 being of the same diameter 'D' as that of the first shank 11, and having a welding lug 15 integral with and projecting from a central zone of an end surface of the second shank 12. The welding lug 15 which will form a break zone 16 as described later has usually a maximum diameter 'd' which is predetermined to be included within a range from 0.5D to 0.8D. Such a dimension is selected here in view of the fact that a drilling and tapping torque necessary for the drill bit and threaded stem portion adjoining it to dig a hole in a workpiece and to subsequently tap the hole is considerably low in general compared with a fastening torque for the turning tight of main portion of the threaded stem. The value of said drilling and tapping torque is equal to, for instance, about one third ($\frac{1}{3}$) to two thirds ($\frac{2}{3}$) of the fastening torque. Thus, said comparatively small diameter 'd' of the welding lug 15 can withstand well a force imparted thereto when drilling and tapping are simultaneously carried out by means of the drill bit and the threaded portion adjoining it, while at the same time allowing these portions to be broken off considerably easily from the main threaded portion.

Figure 3:
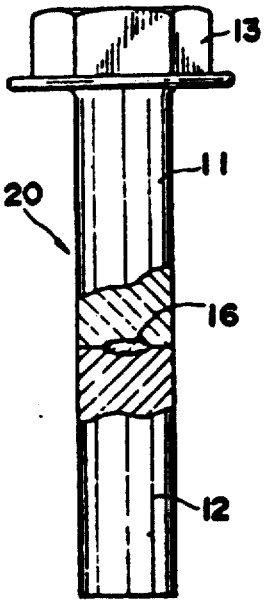
FIG. 3 is a front elevation of a blank.
Figure 4:
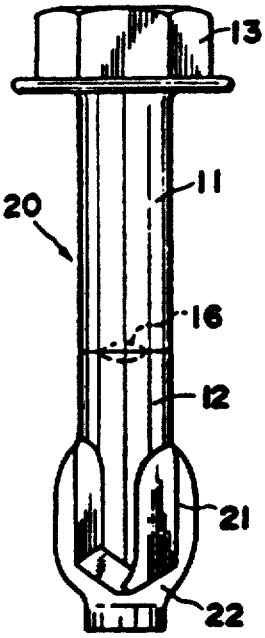
FIG. 4 is a front elevation illustrating a process by which a drill bit is formed.
Figure 5:
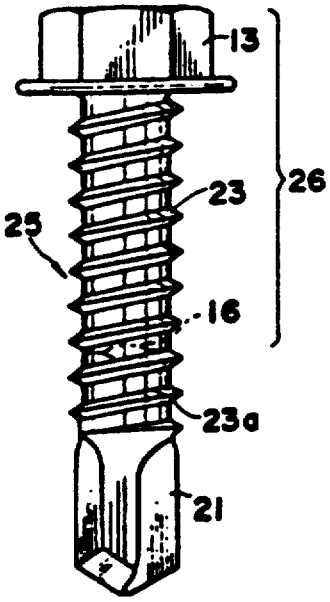
FIG. 5 is a front elevation illustrating a drill screw provided by the present invention.

FIGS. 3 to 5 illustrate a process for manufacturing the drill screw from the first shank 11 and second shank 12.

At first, the flat end surface 14 of the first shank 11 is caused, by projection-welding method, as shown in FIG. 3, to fixedly adjoin the welding lug 15 of the second shank 12 in order that the break zone 16 is formed at bonded portion between said shanks whereby a composite blank 20 is produced.

Next, a drill bit 21 is formed by cold forging of the second shank 12 of the blank 20, as shown in FIG. 4. A machining mold or die used for cold forging of the drill bit 21 is not shown because it is well known in the industry. Such machining will produce a scrap 22 along and projecting from an outer periphery of the drill bit 21.

Subsequently, a continuous screw thread 23 and 23a is formed as shown in FIG. 5 by thread-rolling method employing a known rolling die (not shown) so as to extend around both the outer cylindrical peripheries of the first shank 11 and the second shank 12. The scrap 22 referred to above is removed when the thread-rolling is conducted to form the thread, thereby finishing up the drill bit 21. The threaded portion 23a formed by thread-rolling on the second shank 12 desirably has to extend up to a close proximity to the drill bit 21 so that it comprises at least one pitch of screw thread which shall function as a tapping screw when tapping is done as described below.

A drill screw 25 which has been machined in a manner described above is then subjected to carburizing-and-quenching treatment. This treatment causes carburizing of, i.e., diffusion of carbon into, surface layers of the drill bit 21 and threaded portion 23a which are formed on the second shank 12, to thereby impart a predetermined hardness to said surface layers. However, the threaded portion 23 formed on the first shank 11 is not carburized due to the unsusceptible nature of the metal of which said first shank is made. The break zone 16 located at the bonded or fixedly adjoined portions between the first and second shanks 11, 12 also is not hardened by carburizing-and-quenching since said zone is at an inner part of said shanks.

The drill screw 25 which is manufactured to obtain the above described structure will be used to fasten one object to the other (not shown). After a fastening operation is completed, the drill bit 21 and the threaded portion 23a which are likely to protrude from back surface of the other object are easily broken at the break zone 16 and separated from a remaining main part. A remaining main part 26 comprising the first shank 11 is highly corrosion resistant by virtue of austenitic stainless steel of which said first shank 11 is made.

Although the first shank 11 and the second shank 12 are adjoined to each other by means of projection-welding method (one of resistance welding methods) in the embodiment, they may be bonded or united to each other by any other suitable method such as pressure welding or by use of any suitable adhesive. If it is deemed appropriate for material of said second shank 12 and for character of fastened objects, any other usual hardening or quenching treatment may be utilized in place of the exemplified carburising-and-quenching in order to harden to a satisfactory degree the surfaces of drill bit 21 and threaded portion 23a which are formed from the second shank 12.

What is claimed is:

1. A breakable composite screw comprising: a first shank made of an austenitic stainless steel; a driving head extending from one end of the first shank and engageable with a screw driving tool; a flat surface formed at the other end of the first shank in a direction perpendicular to an axis of the first shank; a second shank made of a [low-carbon steel] *metal susceptible of hardening* and being of the same diameter D as the first shank; a welding lug protruding centrally from an end of the second shank; the second shank being fixedly adjoined to the flat surface by projection-welding by means of the welding lug to thereby provide a break zone at the other end of the first shank; a drill bit formed by cold forging at an end of the second shank; a continuous thread which is formed by thread-rolling so as to extend around both outer cylindrical peripheries of the first shank and second shank wherein a portion extending from the break zone to the drill bit is hardened or quenched.

2. A breakable composite drill screw according to claim 1, in which the welding lug is of a diameter within the range of 0.5D to 0.8D.

*3. A breakable composite drill screw according to claim 1, in which the second shank is made of a low-carbon steel.*

* * * * *